(12) United States Patent
Heid et al.

(10) Patent No.: US 12,097,080 B2
(45) Date of Patent: Sep. 24, 2024

(54) INTERCHANGEABLE LABELLING PLATE

(71) Applicants: AESCULAP INC., Center Valley, PA (US); AESCULAP AG, Tuttlingen (DE)

(72) Inventors: Elmar Heid, Neuhausen (DE); Gerhard Frey, Buchheim (DE); Frank Weller, Markkleeberg (DE); Tommy Schubert, Leverkusen (DE); Edward Nuber, Bethlehem, PA (US)

(73) Assignees: Aesculap Inc., Center Valley, PA (US); Aesculap AG, Tuttlingen (DE)

( * ) Notice: Subject to any disclaimer, the term of this patent is extended or adjusted under 35 U.S.C. 154(b) by 836 days.

(21) Appl. No.: 16/772,323

(22) PCT Filed: Dec. 14, 2017

(86) PCT No.: PCT/US2017/066507
§ 371 (c)(1),
(2) Date: Jun. 12, 2020

(87) PCT Pub. No.: WO2019/117928
PCT Pub. Date: Jun. 20, 2019

(65) Prior Publication Data
US 2021/0077222 A1    Mar. 18, 2021

(51) Int. Cl.
*G09F 3/20* (2006.01)
*A61B 50/33* (2016.01)
(Continued)

(52) U.S. Cl.
CPC ............. *A61B 90/94* (2016.02); *A61B 50/33* (2016.02); *A61L 2/26* (2013.01); *A61L 2202/17* (2013.01);
(Continued)

(58) Field of Classification Search
CPC . A61B 90/94; A61B 50/33; A61L 2/26; A61L 2202/17; A61L 2202/182;
(Continued)

(56) References Cited

U.S. PATENT DOCUMENTS 1,632,537 A * 6/1927 Brigel ................. G09F 1/10
                                                    40/658
1,810,049 A * 6/1931 Hopp ................. G09F 3/202
                                                    40/5
(Continued)

FOREIGN PATENT DOCUMENTS

CN       101371260 A      2/2009
DE       19723857 A1     12/1998
(Continued)

OTHER PUBLICATIONS

International Search Report and Written Opinion for PCT Application No. PCT/US17/66507, dated Feb. 20, 2018, 13 pages.
(Continued)

*Primary Examiner* — Luan K Bui
(74) *Attorney, Agent, or Firm* — CM Law; Christopher A. Rothe

(57) ABSTRACT

A labelling system includes a labelling plate being adapted to be removably connected with a sterile container, wherein the labelling plate includes interfaces for at least one label (e.g. barcode) and at least one identification tag (e.g. RFID). The interfaces can removably hold the at least one identification tag and/or the at least one label at the separate labelling plate.

4 Claims, 1 Drawing Sheet

(51) Int. Cl.
*A61B 90/94* (2016.01)
*A61L 2/26* (2006.01)

(52) U.S. Cl.
CPC ..... *A61L 2202/182* (2013.01); *A61L 2202/24* (2013.01)

(58) Field of Classification Search
CPC .......... A61L 2202/24; G09F 3/16; G09F 3/18; G09F 3/204
USPC ........... 206/438, 459.5; 40/642.02, 649, 652, 40/653, 657–658, 661.11
See application file for complete search history.

(56) References Cited

U.S. PATENT DOCUMENTS

| | | | | |
|---|---|---|---|---|
| 2,634,938 | A * | 4/1953 | Hopp | G09F 3/20 40/648 |
| 4,541,598 | A * | 9/1985 | Villanueva | G09F 3/204 40/658 |
| 4,915,913 | A | 4/1990 | Williams | B65D 45/24 436/1 |
| 5,372,787 | A * | 12/1994 | Ritter | A61B 50/30 206/508 |
| 10,427,841 | B2 * | 10/2019 | Weisshaupt | B65D 43/0204 |
| 2003/0080571 | A1 * | 5/2003 | Schainholz | A61L 2/28 292/310 |
| 2005/0050785 | A1 * | 3/2005 | Byrne | G09F 3/20 40/649 |
| 2006/0162210 | A1 * | 7/2006 | Bauer | G09F 3/20 40/658 |
| 2006/0220865 | A1 | 10/2006 | Babine et al. | |
| 2007/0273520 | A1 | 11/2007 | Chamandy | |
| 2014/0110298 | A1 | 4/2014 | Khajavi | |
| 2014/0259836 | A1 * | 9/2014 | Piccoli | G09F 3/16 29/428 |
| 2015/0225136 | A1 * | 8/2015 | Weisshaupt | B65D 45/20 220/200 |
| 2016/0016165 | A1 | 1/2016 | Provencher et al. | |
| 2019/0298472 | A1 * | 10/2019 | Schuster | A61L 2/07 |

FOREIGN PATENT DOCUMENTS

| | | | |
|---|---|---|---|
| DE | 102004028040 A1 | 10/2005 | |
| WO | 2009003231 A1 | 1/2009 | |

OTHER PUBLICATIONS

Extended European Search Report received in Application No. 17934591.3-1113 dated Jun. 10, 2021, 6 pages.
Office Action received in Chinese Application No. 201780097698.5 dated Dec. 14, 2023, with translation, 14 pages.
Office Action received in Chinese Application No. 201780097698.5 dated Jun. 28, 2024, with translation, 12 pages.
Search Report received in Chinese Application No. 201780097698.5 dated Jun. 28, 2024, with translation, 4 pages.

* cited by examiner

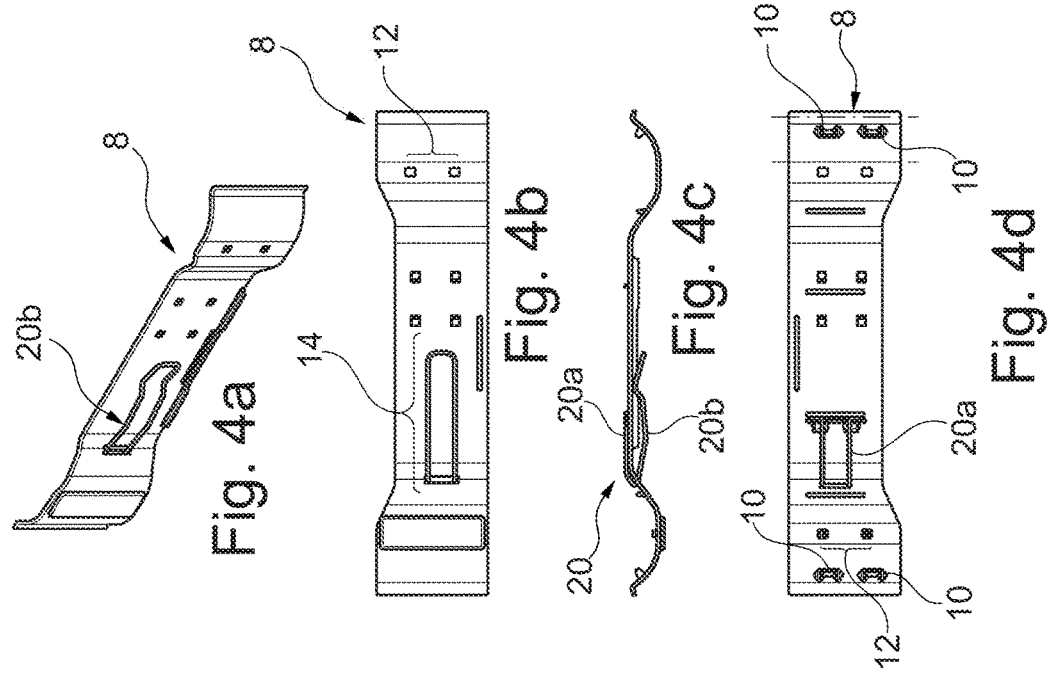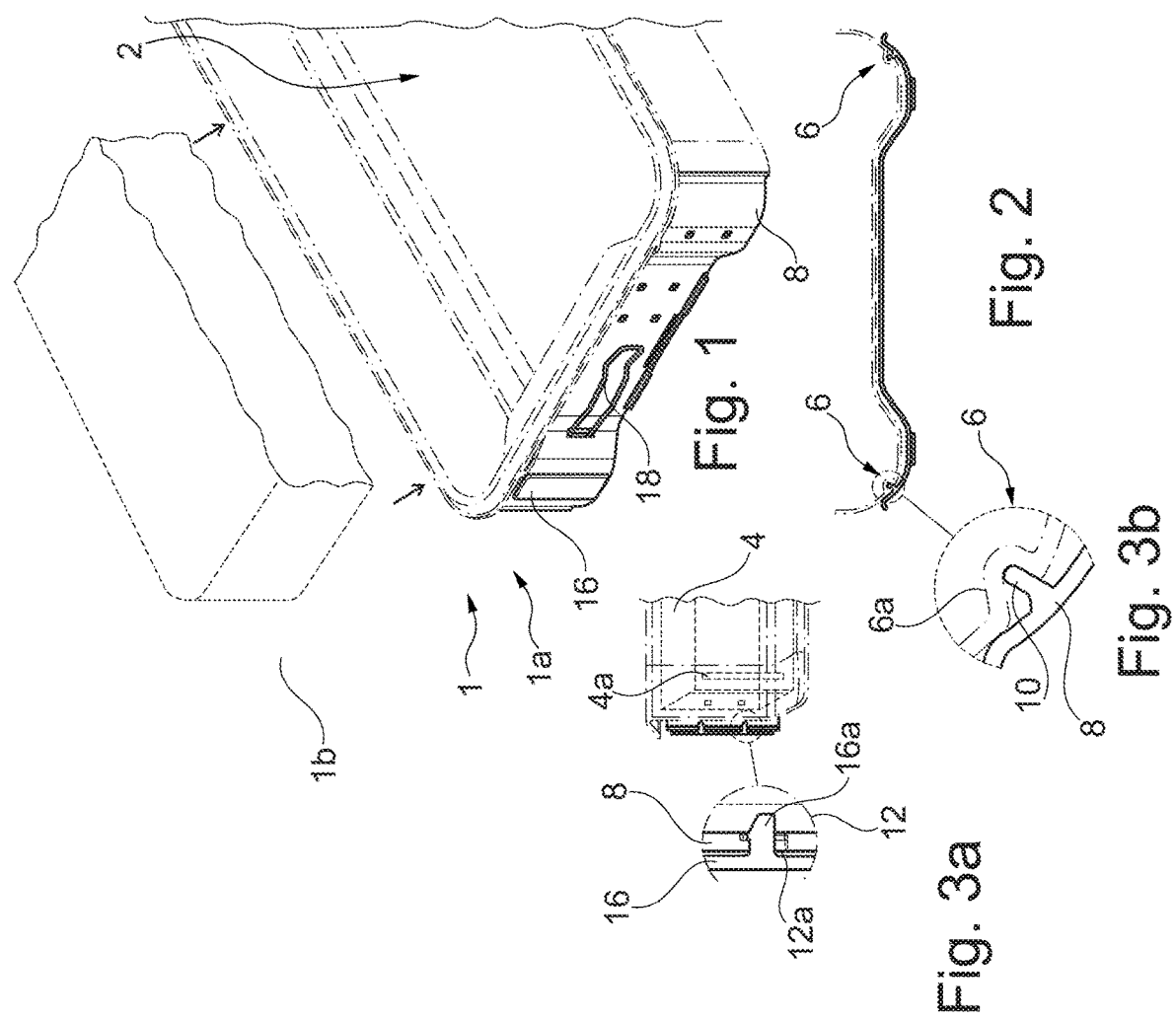

INTERCHANGEABLE LABELLING PLATE

CROSS-REFERENCE TO RELATED APPLICATION

This application is the United States national phase of International Application No. PCT/US2017/066507, filed Dec. 14, 2017, the content of which is incorporated by reference herein in its entirety.

FIELD

The present invention relates to an interchangeable/removable labelling plate for marking/identifying sterile containers and/or instrument trays being removable stored or being storable within the sterile containers.

BACKGROUND

Today, most sterile containers are marked by a combination of barcode labels containing, for example, production data, and/or instrument data like the name of the set/content of the container, etc. and tags (RFID-tags/pucks) preferably made of an aluminium material. In general, at least the tags but in many cases also the labels (containing the barcode and/or alphanumeric information) are firmly fixed with the container, for example, in a window-like device at both ends or opposing side walls of the container. Furthermore, labels are also fixedly connected with the instrument trays being intended and adapted to be stored within the container having the identical label.

The tags may remain on/at the container during cleaning processes with mild alkaline detergents, wherein, however, cleaning processes with high-alkaline cleaning detergents would be more favourable. In the event of a cleaning process with high-alkaline cleaning detergents, however, the problem arises that current aluminium identification tags for performing identification generally do not allow a cleaning in washer-disinfectors using instrument cleaning programs because of missing compatibility with high-alkaline cleaning detergents. Accordingly, in order to solve this problem sterile containers can also be labelled with at least one barcode label (also containing alphanumeric information) only, which can optionally be removed from the container.

The labels used for marking/identifying sterile containers of this kind are generally printed with the relevant data on the clean section of a so-called "sterile processing department" (SPD) and are then glued on the sterile container. The labels can then be optionally removed, for example, in an operation room (OR) and, preferably glued into a patient's documentation. They also can remain on the container or get disposed later on.

In the event of using a sterile container with a firmly fixed identification tag the user on the clean section of the above-mentioned SPO has to wait for the right container to be processed with mild alkaline detergents until he can merge the corresponding instrument tray(s) being processed with high-alkaline cleaning detergents and containers after cleaning and disinfection. This merging process is quite complicate and error-prone.

In the event of using a sterile container with a removable identification tag both the specific sterile container (optionally having the barcode label fixed thereon) and the tag must be processed separately and be connected with each other again in a correct manner. Detachable barcode labels would allow for an individual identification of any container with the respective content, however, they are not linked with the respective set/tray of instruments during the cleaning process. Accordingly, the assignment of the already removed right label and information tag to the right instrument tray is also error-prone.

Finally, the sterile container must be prepared for holding tags and/or labels in a removable manner. This makes the production of such a sterile container complicate and expensive, especially in case that the sterile container shall be prepared to become individually labelled by different labels and/or tags.

SUMMARY

It is an object of the present invention to provide a labelling system and labelling method for sterile containers achieving a higher flexibility especially prior to and after a cleaning process.

Accordingly, one gist of the invention can be seen in the provision of a separate (individual) labelling plate being adapted to be removable connected with a sterile container (and optionally with an instrument tray) wherein the separate labelling plate comprises interfaces (docking/connecting systems) for at least one (barcode) label and at least one (RFID) identification tag. The interfaces are preferably designed for removable holding the at least one tag and/or the at least one label at the separate labelling plate.

In other words, the present invention substantially refers to a labelling system comprising a labelling plate being adapted to be removable connected with a sterile container (using an uniform labelling plate connecting/catch mechanism) wherein the labelling plate comprises (a plurality of individual) interfaces for at least one (barcode) label and at least one (RFID) identification tag, wherein the interfaces on the labelling plate are designed for removable/detachable holding the at least one tag and/or the at least one label at the separate labelling plate.

By the provision of such a labelling plate, the sterile container can be manufactured with exclusively one single/uniform/standard interface for the (one) labelling plate, which contributes to keep the manufacturing costs low, wherein the separate labelling plate is equipped with a plurality of individual interfaces for the tag(s) and the label(s) which contributes to keep the flexibility in handling the sterile container high.

According to an optional aspect of the present invention the at least one interface of the labelling plate is/comprises a (retaining) clip or brace. The clip is advantageously designed like a paper-clip wherein the one clip leg is fixedly connected with the labelling plate and the other clip leg is elastically movable relative to a front side of the labelling plate to clamp, for example, a plate- or card-like label between the movable clip leg and the front side of the labelling plate.

According to another optional aspect of the present invention the at least one other interface of the labelling plate comprises at least one retaining hole or recess being adapted to (removable) receive an elastically deformable tag connection/catch mechanism, for example, in the form of a hook-like cone, engaging pawl or notch, which mechanism is formed/provided at the tag. Therefore, the tag can be pressed or clicked onto the front side of the labelling plate (parallel to the label) wherein the cone or cones are inserted into the hole(s) on the front side of the labelling plate thereby generating preferably a form fit.

According to another optional aspect of the present invention the labelling plate has an uniform plate connection/catch mechanism, for example in the form of elastically movable/deformable hooks, cones or borders which are adapted to get removable engaged with the single/uniform/standard plate interface, especially recesses or grooves, (uniformly) formed/provided at the sterile container to be marked. Alternatively thereto, an adapter element can be provided which is (individually) adapted to get fixed at a sterile container of known design, wherein the adapter element comprises the (uniform) plate interface (recesses/grooves) for the labelling plate.

Another gist of the invention can be seen in the provision of a sterile container comprising a basis pan/trough (lower shell) and a lid/cover (upper shell) which are connectable with each other to form a closed container compartment for accommodating instrument tray(s) therein.

According to the invention the sterile container, especially its basis pan/trough has an uniform plate interface, especially at least one or a plurality of recesses or grooves being adapted to removable receive the plate connection/catch mechanism, especially the hooks or borders of the labelling plate as defined above (such that the labelling plate can be temporarily connected to the tray by form fit).

Another gist of the invention can be seen in the provision of a sterile container set comprising the labelling plate and the sterile container as defined above.

According to an optional aspect of the present invention the sterile container set further comprises at least one instrument tray adapted to be accommodated within the container compartment, wherein the tray has an uniform plate interface, especially at least one or a plurality of recesses or grooves, wherein the plate interface of the tray is adapted to removable receive the plate connection/catch mechanism, especially the hooks or borders of the labelling plate as defined above such that the labelling plate can be temporarily connected to the tray (for example during a disinfection process).

Another gist of the invention can be seen in the provision of a labelling method for sterile containers especially in the event of disinfection processing cycles comprising the following method steps:
 (Temporarily) fixing a transparent or coloured labelling plate (according to the above definition) on/at a sterile container (by use of the click-on mechanism as described above) preferably inside the clean section of a SPD as defined above,
 (Temporarily) adding at least one tag and at least one (batch control) label on the front side of the labelling plate at the corresponding interfaces being provided thereon,
 processing the thus labelled and sterilized sterile container and instrument set contained therein to/in the operation room wherein the (barcode carrying) label could be at least partially removed and fixed, for example, into the patient's documentation and/or parts of the labelling could be disposed),
 processing back the sterile container to the SPD after its use in the operation room,
 opening the sterile container in the SPD and removing the used instrument tray,
 removing the labelling plate from the sterile container, removing the tag from the labelling plate and connecting the labelling plate (optionally including the labels) with the used instrument tray contained in the sterile container for processing the tray and the labelling plate together in a washer/disinfector,
 merging the cleaned instrument tray together with any cleaned sterile container (having the correct size),
 removing the labelling plate from the cleaned instrument tray and connecting the same with the sterile container and
 connecting the tag (being cleaned separately to the sterile container and instrument tray) to the labelling plate.

BRIEF DESCRIPTION OF THE DRAWING FIGURES

The present invention will be described in more detail below on the basis of a preferred embodiment by reference to the enclosed figures, according to which:

FIG. 1 shows a lower shell of a sterile container already equipped with a labelling plate according to an embodiment of the present invention in a perspective view, wherein an upper shell can have substantially the same shape and is, therefore, not individually shown anymore[[,]];

FIG. 2 shows a length section of the labelling plate in a connected state with the sterile container;

FIGS. 3*a* and 3*b* show a tag connection/catch mechanism and a plate connection/catch mechanism in enlarged view, respectively FIGS. 4*a* to 4*d* show the labelling plate according to an embodiment in different views being equipped with an (one) information tag.

DETAILED DESCRIPTION

According to FIG. 1, a lower shell (or basis pan/trough) 1*a* of a sterile container 1 is shown in detail forming a container compartment 2 into which a tray 4 as indicated in FIG. 3*a* can be inserted wherein the lower shell 1*a* can be air-tightly closed by an upper shell 1*b* (as indicated in FIG. 1) which may have a shape substantially similar to the lower shell.

In the preferred embodiment the lower shell 1*a* comprises a plate receiving interface 6 preferably in the form of two parallel distanced groove-like recesses 6*a* being pressed into a side wall of the lower shell 1*a*. Alternatively, instead of grooves also hole-like recesses could be formed. Besides, instead of or in addition to the lower shell 1*a* also the upper shell 1*b* could be formed with a plate receiving interface 6 of this kind.

In general, the plate receiving interface 6 is intended to have a standard or uniform shape at each sterile container 1 being manufactured in future. In case of already existing sterile containers an adapter element (not shown) could be provided which is connectable to the (existing) sterile container, for example by gluing or welding, and which has the (standard) receiving interface 6 on its free side.

As can be seen in FIGS. 4*a* and 4*b*, a (separate) labelling plate 8 is provided which is substantially adapted in its outer shape to the side wall of the sterile container 1 such that it can be attached to the side wall of the sterile container 1 (lower shell 1*a*) in a tight manner. In order to achieve a fixed but detachable connection between the sterile container 1 and the labelling plate 8 at least two (preferably four) parallel extended borders or hooks 10 are formed thereon representing a plate connection or catch mechanism which are designed to elastically engage with the recesses 6*a* of the sterile container 1. As can be seen especially in FIG. 3*b*, each recess 6*a* of the sterile container 1 forms an undercut into which the borders or hooks 10 are elastically pressed to hold the labelling plate 8 at the side wall of the container 1 substantially by form fit.

The labelling plate 8 comprises at least two interfaces 12, 14 at its (free) front side which are adapted to detachably hold at least one information tag 16 and at least one card-like label 18. As can be seen especially in FIG. 3a the one interface 12 for the information tag 16 comprises preferably two holes or recesses 12a forming undercuts respectively. The information tag 16, therefore, comprises a tag connection/catch mechanism, preferably in the form of, for example two cone-like (notch-like) protrusions 16a which are elastically deformable and which are designed to engage with the holes or recesses 12a at the labelling plate 8 such that a detachable form fit is generated in between.

According to FIGS. 4a and 4b, the other interface 14 for the label 18 comprises a clip or brace (preferably in the form of a paper clip) 20 having two clip legs 20a, 20b wherein one clip leg 20a is fixedly connected with the labelling plate 8 and the other one 20b is freely hold above/along the front side of labelling plate 8 such that the label 18, for example in the form of a credit card, can be sandwiched between the freely hold clip leg 20b (being elastic) and the front side of the labelling plate 8.

It shall be pointed out here, that the labelling plate 8 may have more interfaces for additional information tags and/or labels which are just indicated in the front side of the labelling plate 8 by through holes as shown especially in FIGS. 4c and 4d.

With the labelling system comprising the labelling plate 8 the information tag 16 and the label 18 as described above the interchangeable (front) labelling plate 8 for tags and (barcode) labels is used made from materials which are compatible with reprocessing methods in sterile processing like stainless steel, plastic like PEEK or PPSU, etc. (irrespective to the materials of the tag and/or the label). Accordingly the use of such a labelling system in processing cycles for disinfection is as follows (starting in the clean section of the SPD):

A transparent or coloured labelling plate 8 is (detachably) fixed on/at the sterile container 1 (preferably its lower shell 1a) wherein the click-on mechanism as described above is used.

Additional smaller identification tag(s) 16 and (batch control) label(s) 18 are added on the front side of the labelling plate 8 using the at least two (individual) interfaces 12, 14 provided thereon.

The thus labelled and sterilized container 1 (into which an instrument tray 4 was inserted before) are then processed to an operation room for its use.

In the operation room (barcode) labels 18 can be removed and, for example, be glued into the patient's documentation. Also at least parts of the labels 18 can be disposed. Alternatively, at least parts of the labels 18 can be maintained at the sterile container 1 after use.

After use in the operation room the sterile container 1 is generally processed back to the SPD.

In the SPD the container 1 is opened and the used instrument tray(s) 4 is/are removed from the sterile container 1.

The instrument tray(s) can then be processed together with the already removed labelling plate 8, for example, in a washer/disinfector. Here, the labelling plate 8 can optionally be connected to the instrument try 4 at the respective (uniform) interface 4a being provided at the tray 4 and having the same shape and size than the plate interface 6 at the sterile container 1.

After the cleaning process is finished the instrument tray(s) 4 is/are merged together with any container (having the right size) because the containers are un-labelled at this stage.

Finally, the labelling plate 8 which has been processed together with the tray(s) 4 is connected on the selected (available) sterile container 1 into which the tray(s) 4 is/are inserted.

The above-described procedure allows at any time during the sterile processing cycle to identify the content of an instrument set inside and outside the container. At the clean section of the sterile processing department (SPD) any container of the right size can be used for merging with an instrument tray regardless its former content.

Different from using single use barcode labels the identification of the instrument tray during cleaning and disinfection is possible because the labelling plate holding the label can be connected at the instrument tray for the cleaning process.

The use of different additional tags on the labelling plate allows also the break-up of the content of the sterile container into different instrument trays for cleaning and disinfection.

The invention claimed is:

1. A labelling plate adapted to be removably connected to a sterile container, the labelling plate comprising interfaces for at least one label and at least one identification tag, the interfaces comprising a first interface and a second interface, the first interface and the second interface designed for removably holding at least one of the at least one label and the at least one identification tag on the labelling plate, wherein the first interface is or comprises a retaining clip or brace, wherein the retaining clip or brace has a shape of a paper clip comprising a fixed clip leg fixedly connected with the labelling plate and a movable clip leg elastically movable relative to a front side of the labelling plate to be able to clamp the at least one label between the movable clip leg and the front side of the labelling plate, the labelling plate further comprising a slot extending through the labelling plate, wherein the retaining clip or brace extends through the slot such that the movable clip leg is positioned on the front side of the labelling plate and the fixed clip leg is positioned on a rear side of the labelling plate opposite the front side of the labelling plate.

2. A labelling plate adapted to be removably connected to a sterile container, the labelling plate comprising interfaces for at least one label and at least one identification tag, the interfaces comprising a first interface and a second interface, the first interface and the second interface designed for removably holding at least one of the at least one label and the at least one identification tag on the labelling plate, wherein the first interface is or comprises a retaining clip or brace, wherein the retaining clip or brace has a shape of a paper clip comprising a fixed clip leg fixedly connected with the labelling plate and a movable clip leg elastically movable relative to a front side of the labelling plate to be able to clamp the at least one label between the movable clip leg and the front side of the labelling plate, wherein the labelling plate further comprises a slot extending through the labelling plate, wherein the retaining clip or brace extends through the slot such that the movable clip leg is positioned on the front side of the labelling plate and the fixed clip leg is positioned on a rear side of the labelling plate opposite the front side of the labelling plate, and wherein the first interface comprises a convex section along the front side of the labeling plate, and the second interface comprises a planar section along the front side of the labeling plate.

3. The labelling plate according to claim 2, wherein the slot extends through the convex section, and the movable clip leg extends along the planar section.

4. A labelling plate adapted to be removably connected to a sterile container, the labelling plate comprising interfaces for at least one label and at least one identification tag, the interfaces comprising a first interface and a second interface, the first interface and the second interface designed for removably holding at least one of the at least one label and the at least one identification tag on the labelling plate,
 wherein the first interface is or comprises a retaining clip or brace,
 wherein the retaining clip or brace comprises a fixed clip leg fixedly connected with the labelling plate and a movable clip leg elastically movable relative to a front side of the labelling plate to be able to clamp the at least one label between the movable clip leg and the front side of the labelling plate,
 the labelling plate further comprising a slot extending through the labelling plate, wherein the retaining clip or brace extends through the slot such that the movable clip leg is positioned on the front side of the labelling plate and the fixed clip leg is positioned on a rear side of the labelling plate opposite the front side of the labelling plate.

* * * * *